United States Patent
Vasänge et al.

[11] Patent Number: 6,124,266
[45] Date of Patent: Sep. 26, 2000

[54] SULPHOLIPID COMPOSITION AND METHODS FOR TREATING SKIN DISORDERS

[75] Inventors: Mervi Vasänge; Wenche Rolfsen; Lars Bohlin, all of Uppsala, Sweden

[73] Assignee: Scotia Lipid Teknik AB, Stockholm, Sweden

[21] Appl. No.: 09/171,939

[22] PCT Filed: Apr. 30, 1997

[86] PCT No.: PCT/SE97/00735

§ 371 Date: Apr. 27, 1999

§ 102(e) Date: Apr. 27, 1999

[87] PCT Pub. No.: WO97/40838

PCT Pub. Date: Nov. 6, 1997

[30] Foreign Application Priority Data

May 2, 1996 [SE] Sweden ............................... 9601677

[51] Int. Cl.$^7$ ............................................. A61K 31/70
[52] U.S. Cl. ................................. 514/24; 514/886; 514/887
[58] Field of Search ........................... 424/195.1, 59, 424/60; 514/24, 887, 886

[56] References Cited

U.S. PATENT DOCUMENTS 5,614,197 3/1997 Pathak et al. .................... 424/195.1
5,620,962 4/1997 Winget .............................. 514/25

FOREIGN PATENT DOCUMENTS 3-52815 3/1991 Japan .
3-52816 3/1991 Japan .

OTHER PUBLICATIONS

Vasange, et al., "A Sulphonoglycolipid from the Fern *Polypodium decumanum* and its Effect on the Platelet Activating-factor Receptor in Human Neutrophils," *J. Pharm. Pharmacol.*, 49, 562–566 (1997).

Morimoto, et al., "Studies on Glycolipids. VII.$^{1)}$ Isolation of Two New Sulfoquinovosyl Diacylglycerols from the Green Alga *Chlorella vulgaris*," *Chem. Pharm. Bull.* 41(9) 1545–1548 (1993).

Gustafson, et al., "AIDS–Antiviral Sulfolipids From Cyanobacteria (Blue–Green Algae)," *Journal of the National Cancer Institute*, 81(16) 1254–1258 (1989).

*Primary Examiner*—Marianne M. Cintins
*Assistant Examiner*—Vickie Kim
*Attorney, Agent, or Firm*—Hoffmann & Baron, LLP

[57] ABSTRACT

The invention refers to the use of a sulpholipid SQDG having formula (I), wherein $R_1$ and $R_2$, which are the same or different, are hydrogen or saturated or unsaturated, optionally hydroxy-substituted acyl groups, protonated or as a salt, for the preparation of a pharmaceutical composition for the treatment of inflammatory skin diseases or disorders, especially psoriasis. A pharmaceutical composition comprising an SQDG compound in combination with a polyunsaturated fatty acid and a therapeutically acceptable carrier is also described.

(I)

$$\begin{array}{l} CH_2OR^1 \\ R^2OCH \\ CH_2O\text{-deoxyhexose-}SO_3H \end{array}$$

8 Claims, 2 Drawing Sheets

SULPHOLIPID COMPOSITION AND METHODS FOR TREATING SKIN DISORDERS

The present application is a U.S. National application filed under 35 USC 371 of PCT/SE97/00735, filed Apr. 20, 1997.

A SULPHOLIPID COMPOSITION AND METHODS FOR TREATING SKIN DISORDERS

The present invention refers to a new PAP-receptor antagonist, the sulpholipid SQDG, as well as to the use of SQDG for the prophylaxis or treatment of inflammatory skin diseases, especially psoriasis.

BACKGROUND OF THE INVENTION

Inflammatory skin diseases such as atopic dermatitis, urticaria and especially psoriasis still constitute a great problem for the affected patients as there are today no effective therapies.

Psoriasis is a common chronic inflammatory dermatosis with a global distribution; it has been estimated that about 1.5% of the population in the western countries can be expected to suffer from the disease during their lifetime. A number of different clinical patterns of psoriasis are acknowledged, the most common being plaque psoriasis.

Hyperproliferation, inflammation with massive infiltration of leucocytes and disturbances in cell differentiation are the typical characteristics of psoriatic skin. The number of basal cells is vastly increased which reduces the turn-over time for the epidermis from the normal 27 days to 3–4 days. The normal events of cell maturation and keratinization do not occur. This proliferation of keratinocytes occurs both in involved and non-involved psoriatic skin but is most pronounced in the plaques. The inflammatory infiltrate from psoriatic lesions has been found to consist predominantly of mononuclear T lymphocytes. There is a disturbed T cell function also in the circulating blood, which implies a possible cell-mediated immunological abnormality in psoriasis. The phagocytes that can be identified histologically in the psoriatic lesion, neutrophils in particular, suggest a role for the chemotactic inflammatory mediators in the pathology of psoriasis. Among these interleukin-1, -6 and -8, leukotriene $B_4$ and PAF have been isolated in pathological amounts in the affected skin.

There is a number of different therapies of psoriasis of varying effectiveness, none being perfect. Among the antipsoriatic drugs of natural origin can be mentioned coal tar, dithranol, psoralens, retinoids and cyclosporin A. In addition to said more established therapies can also be mentioned the use of podophyllotoxin, a lignan which can be isolated from Podophyllum species, polyunsaturated fatty acids, such as eicosapentaenoic acid and gammalinolenic acid, and colchicine, an alkaloid from the crocus plant. The use of essential fatty acids in atopic dermatitis and psoriasis, respectively, are described by Wright, S., British Journal of Dermatology 125, 503–515, 1991.

In the traditional medicine of Honduras the name Calaguala is used for the extract of a number of closely related Polypodium species, including *P. decumanum Willd., P. aureum* (or *P. leucatomos*), *P. lowei C. Chr., P. loriceum L., P. triseriale Sw., P. fraxinifolium Jacq.* and *P. dissimile L* (Molina, personal communication, 1991). A decoction or infusion of the Calaguala plant has been used to treat a number of diseases including peptic ulcer, kidney problems, diarrhoea and arthritis or other pains in joints and tendons.

Over the last two decades several clinical trials have been performed on calaguala in the treatment of psoriasis, as well as atopic dermatitis (Vargas Gonzales, J. P., et al., Acta Pediatric. Esp. 46(1), 556–561, 1988) and vitiligo (Gonzales, S., et al., J. Invest. Derm. 102(4), 651, 1994).

Platelet activating factor (PAF; 1-O-alkyl-2-acetyl-sn-glycero-3-phosphocholine) is a phospholipid derived mediator with a diversity of biological effects. PAF is released from various cell types, including platelets, neutrophils, monocytes and endothelial cells. In addition, several cell types, including neutrophils, are known to express specific PAF receptors on their cell membrane. In vitro PAF exhibits effects, including aggregation and degranulation of leukocytes and inhibition of lymphocyte proliferation. In vivo effects include hypotension, acute renal failure and increase in vascular permeability. PAF is thought to be associated with a number of pathological conditions, such as shock, airway hypersensitivity and asthma, inflammation of many different types, psoriasis, arthritis and graft rejection and various cardiovascular disorders especially ones associated with thrombosis, blood coagulation and platelet aggregation.

A large number of natural and synthetic PAF receptor antagonists has been discovered which show different physiological effects, but to date they have been of limited usefulness for pharmaceutical purposes. The use of some compounds in the treatment of asthma is, however, currently being evaluated. As the PAF antagonist therapy is relatively new, more research is still needed for the judgement of therapeutic benefit for specific indications. It is believed that safe and potent compounds will have a substantial role in therapeutical treatments.

Perhaps the best known of all PAF antagonists is the ginkgolide BN 52021 which was isolated from the "fossil tree" Ginkgo biloba in the late 60's. It is a specific PAF receptor antagonist and has shown anti-inflammatory properties in several in vivo and in vitro models. For the potential oral treatment of chronic inflammatory diseases, the synthetic hetrazepine derivative BN 50730 was later developed. It shows a several ten-folds more potent PAF antagonistic activity in vitro. (Guinot, P. in Clinical Reviews in Allergy 12, 397–417, 1994.)

It has been suggested that PAF contributes to the inflammatory aspects of psoriasis (Cunningham, 1990). Factors that implicate its role in the pathogenesis and symptoms are that PAF has been isolated in elevated amounts on psoriatic skin, that injection of PAF causes vasodilation and increased vascular permeability, and that PAF is chemoattractant mainly to neutrophils.

Recently, PAF activity has been measured in blood plasma of patients with psoriasis using a radioimmunoassay technique (Izaki et al., British Journal of Dermatology 136, 1060–1064, 1996). It was shown that levels of PAF were significantly elevated in patients with psoriasis and that when these patients were treated with conventional antipsoriatic methods the levels were decreased. Also, the decrease was correlated with a clinical improvement. It is concluded that PAF has a role in the acute phase of psoriatic and leucotactic inflammation.

In another study, chemotactic responsiveness of pheripheral blood eosinophils from healthy subjects and from patients with inflammatory dermatoses (psoriasis, atopic dermatitis) was determined. It was found that chemotactic responsiveness was significantly enhanced in severely affected patients and that this increase was not related to a specific disease. The increased responsiveness in peripheral eosinophils to PAF is suggested to be related to altered receptor expression during cutaneous inflammation (Morita et al. 1989).

PRIOR ART

The sulphoquinovosyldiacylglycerols, SQDG, constitute one of the four major classes of polar lipids in chloroplast membranes of most photosynthetic organisms. They are structural components of the thylakoid membrane and are involved in the electron transport chain in photosynthesis as well as in the construction of chloroplasts.

In Chem. Pharm. Bull. 41 (9), 1664–1666, 1993, Shirahashi et al. describe the isolation and identification of anti-tumour-promoting principles from an extract of the cyanobacterium Phormidium tenue. Said extract turned out to comprise three classes of glycolipids, that is monogalactosyldiacylglycerol (MGDG), digalactosyldiacylglycerol (DGDG) and sulphoquinovosyldiacylglycerol (SQDG). MGDG and DGDG turned out to inhibit tumour promotion more intensely than SQDG, or rather a mixture of different SQDGs.

The Journal of the National Cancer Institute, Vol. 81, No. 16, Aug. 16, 1989, Gustafson et al., refers to the isolation and identification of four anti-HIV active sulpholipids from cyanobacterial extracts by a combination of gel-permeation and reversed-phase chromatographies. The sulpholipids all had similar levels of activity.

JP patent application No. 64-186626 discloses the use of a sulphonoglycolipid, an SQDG of the formula

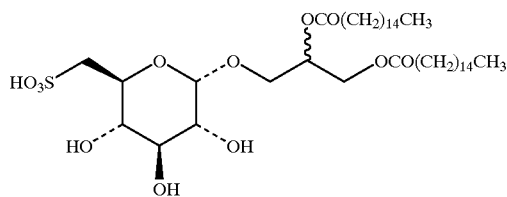

to obtain a remedy for intravascular blood coagulation syndrome, and JP patent application No. 64-186627 describes the use of the same compound in the treatment of nephritis.

DESCRIPTION OF THE INVENTION

The present invention refers to the use of an SQDG having the formula

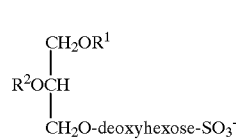

(I)

wherein $R^1$ and $R^2$, which are the same or different, are hydrogen or saturated or unsaturated, optionally hydroxy-substituted acyl groups, protonated or as a salt, for the preparation of a pharmaceutical composition for the treatment of inflammatory skin diseases or disorders.

A preferred SQDG to be used according to the invention is a sulphoquinovosyldiacylglycerol having the formula

(II)

wherein $R^1$ and $R^2$, which are the same or different, are hydrogen, acetyl or acyl groups comprising 14–22 carbon atoms, preferably 16–18, and having up to 6 unsaturations, preferably 0–3.

As examples of acyl groups $R^1$ and $R^2$ can be mentioned fatty acid residues such as palmitoyl, stearoyl, oleoyl, linoleoyl, γ-linolenoyl, columbinoyl, dihomo-γ-linolenoyl, arachidonoyl, eicosapentaenoyl, docosahexaenoyl and ricinoloyl, as well as conjugated forms thereof.

The invention specially refers to the use of a 1,2-O,O-dipalmitoyl-[6'-sulpho-α-D-quinovopyranosyl(1'→3)]-sn-glycerol, an SQDG having the formula

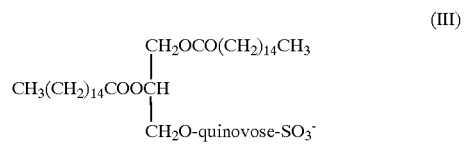

(III)

protonated or as a salt.

Whenever applicable, the expression "an SQDG" is also intended to comprise a salt of SQDG, for instance a sodium, potassium or ammonium salt, or a mixture of one or more SQDG compounds. The counterion can also be a cationic lipid or another organic cation to form an SQDG derivative being a prodrug. The SQDG compounds may be isolated from nature as such or may be chemically modified to introduce different acyl groups with specific valuable properties. Examples of modifications are partial or total hydrolysis of acyl groups, partial or total hydrogenation, regioselective desaturation and inter- or transesterification. In natural SQDGs the quinovosyl is always in position 3 of the glycerol and has the D-form. The glycosidic link in general has the α-form.

Especially, the SQDG can be used according to the invention for the prophylaxis or treatment of atopic dermatitis, urticaria and psoriasis.

Another use of an SQDG according to the invention is as an antiproliferative agent.

A preferred use of an SQDG according to the invention is for the prophylaxis or treatment of psoriasis.

Another preferred use of an SQDG according to the invention, is in combination with a mono- or polyunsaturated fatty acid for the prophylaxis or treatment of psoriasis. In this combination the fatty acids can be in the form of free fatty acids, monoacylglycerols, diacylglycerols or triacylglycerols, for example a marine oil or evening primrose oil.

Mono-unsaturated fatty acids preferably comprise 16–22 carbon atoms, and can for instance be oleic acid.

The polyunsaturated fatty acid, PUFA, to be used in combination with the SQDG should preferably comprise 18–22 carbon atoms and 2–6 unsaturations, and can for instance be an essential fatty acid of the n-6 or n-3 family. Examples of n-6 acids are γ-linolenic acid, dihomo-γ-linolenic acid, arachidonic acid. Examples of n-3 acids are α-linolenic acid, octadecatetraenoic acid, eicosatetraenoic acid, eicosapentaenoic acid, docosapentaenoic acid and docosahexaenoic acid.

In the treatment of atopic dermatitis the fatty acids are preferably chosen among γ-linolenic acid, dihomo gamma-linolenic acid and arachidonic acid. In the treatment of psoriasis the fatty acids are preferably chosen among α-linolenic acid, octadecatetraenoic acid, eicosatetraenoic acid, eicosapentaenoic acid, docosapentaenoic acid and docosahexaenoic acid.

The invention also refers to a pharmaceutical composition comprising an SQDG having the formula

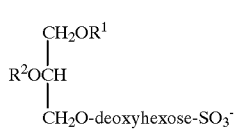

(I)

wherein $R^1$ and $R^2$, which are the same or different, are hydrogen or saturated or unsaturated, optionally hydroxy-substituted acyl groups, protonated or as a salt, in combination with a polyunsaturated fatty acid and a therapeutically acceptable carrier for the treatment of dermal diseases, especially psoriasis.

The pharmaceutical composition preferably comprises an SQDG having the formula II or III as described above.

Therapeutically acceptable carriers are for instance conventional carriers for solutions, suspensions, liposomes, emulsions, aerosols, topical preparations, powders, granules, tablets, capsules or suppositories.

Said pharmaceutical composition can be orally, topically, ocularly, nasally, aurally, vaginally, rectally, enterally or parenterally administrated.

In oral administration the administered dose could be from 1 to 100 mg/d, preferably 2–25, especially 2–15 mg/d. In topical application the administered dose should be at least ten times the oral dose giving a preferred range of 10–200 mg/cm$^2$/d. The injected amount of the active substance could be estimated to 0.1 to 10 mg/d.

The invention also refers to a new PAF-receptor antagonist, characterized in being an SQDG having the formula

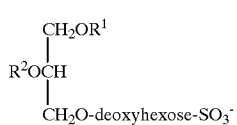

(I)

wherein $R^1$ and $R^2$, which are the same or different, are hydrogen or saturated or unsaturated, optionally hydroxy-substituted acyl groups, protonated or as a salt.

SQDG can be obtained from natural sources, such as green plants, plant tissues, sponges, bacteria or algae by drying, such as air drying or lyophilization, extraction and subsequent purification by chromatographic or other methods. In cases where chemical modification of the obtained material is performed, further purification may be necessary to obtain the desired compound. In this application SQDG was obtained by preparing a methanolic extract of the plant material which was subsequently subjected to repeated straight phase column chromatography on silica gel with chloroform and methanol as eluents. Fractions containing polar lipids were then further purified on Sephadex LH20 with water, methanol and ethanol mixtures.

Isolation of SQDG From Polypodium Decumanum

Figure 1:
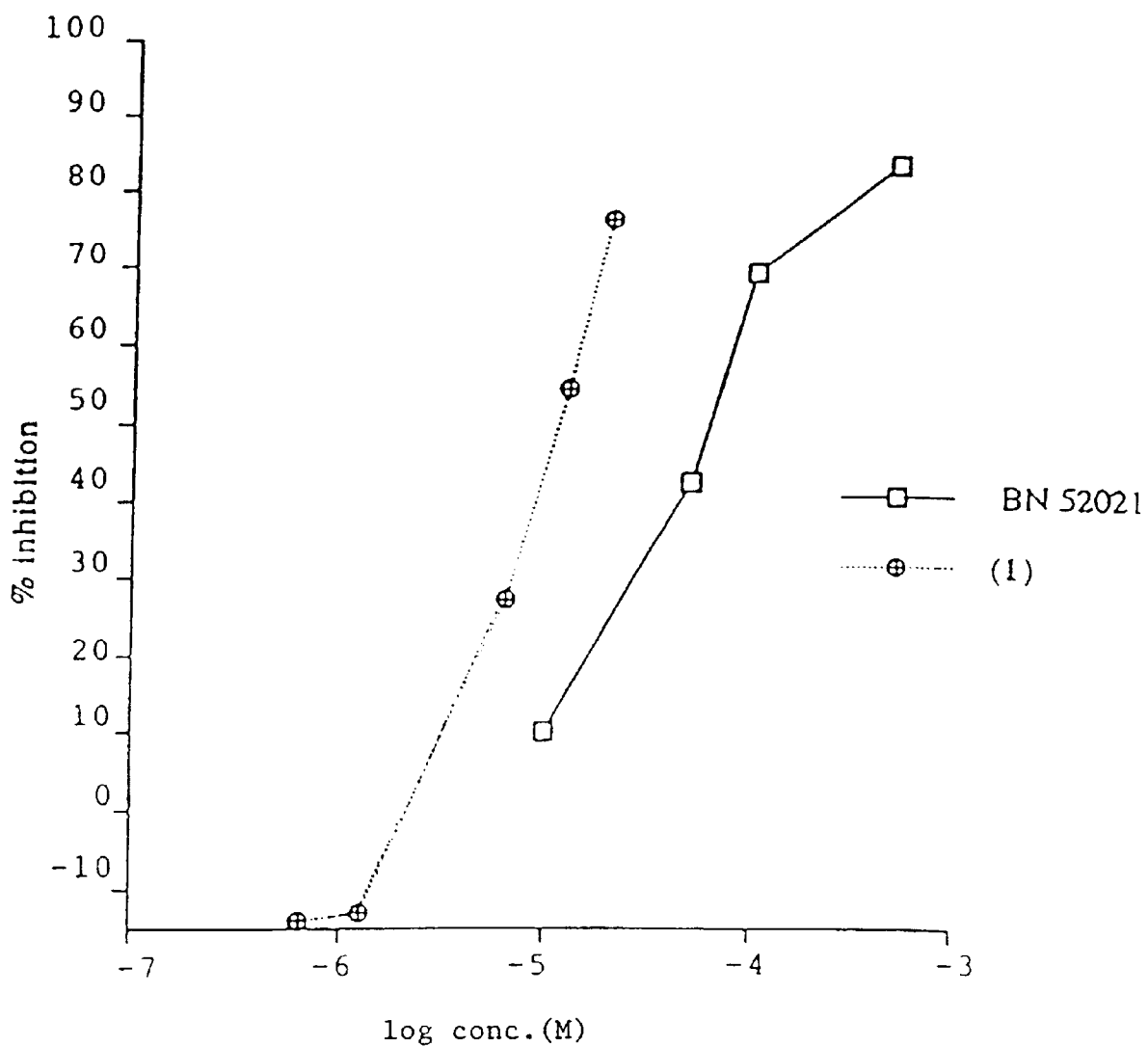
FIG. 1 shows the dose response curve of the SQDG of the formula III, and of the PAF receptor antagonist ginkgolide BN 52021.

The plant material for preparing the Calaguala extract was obtained from a plantation near the Lago de Yohoa in Honduras. Polypodium decumanum is a fern which in its natural environment grows as an epiphyte on palm trees, but which is also cultured for its beneficial pharmacological effects.

The dried and ground leaves (6.6 kg) were extracted with 3×35 1 methanol (puriss) overnight under stirring at room temperature. The extract was filtered, concentrated in vacuo and lyophilised (yield 267 g). 50 g of the methanolic extract was then dissolved in 400 ml water and extracted with 4×600 ml chloroform; yield 16 g. The chloroform extract was adsorbed on silica gel (Merck, mesh 70–230) and eluted through a column packed with 200 g silica gel using a gradient of chloroform to methanol. Fractions of 20 ml were collected and pooled together according to TLC comparison. 10 fractions were obtained and checked for activity in the elastase assay described below. The most active fractions (1.8 g) were repeatedly chromatographed on silica gel with a gradient of chloroform to methanol and the combined active fractions (1.4 g) were then eluted through a Sephadex LH 20 column (Pharmacia Fine Chemicals, Sweden) with a gradient of methanol (30%) and water to 100% methanol as mobile phase. The next to the last fraction (210 mg) showed the highest activity in the assay and was further purified using a second Sephadex LH 20 column which was first washed with ethanol and then eluted with methanol. By this 10 mg of the compound 1,2-O,O-dipalmitoyl-[6'-sulpho-α-D-quinovopyranosyl(1'→3) ]-sn-glycerol, that is a compound of the formula III above, was obtained. The structure of the compound was verified as below.

Identification of the SQDG Compound

The structure of the compound was identified by means of mass spectrometry, carbohydrate analysis and NMR.

GC-MS analysis was done on a HP 5890 gas chromatograph coupled to a HP 5970A quadruple mass selective detector operated at an ionization voltage of 70 eV and an electron multiplier voltage of 1800 V. The compound was analyzed after a transesterification reaction according to Seppanen-Laakso, T., et al., Acta Pharm. Fenn. 99, 109–117, 1990, which allows the identification of bound fatty acids. A single peak was observed in the GC chromatogram and the peak exhibited major signals at m/Z (M+) 239, 227, 213, 199, 185, 157, 143, 129, 97, 87, 74, 59, 43 and was thus identified as the methylester of palmitic acid. For the molecular weight determination a positive ion FAB mass spectrum was recorded with a JEOL SX 102 instrument with glycerol as matrix. By this a molecular ion [M+1]$^+$ at m/z=817 was displayed corresponding to a molecular formula of $C_{41}H_{77}O_{12}SNa$ for the compound.

Carbohydrate analysis was performed by hydrolysing the compound with trifluoroacetic acid followed by reduction and acetylation and the resulting peracetylated compound was compared by gas chromatography with authentic carbohydrates treated in the same manner. This comparison yielded glucose.

The NMR experiments were run using a JEOL 270 MHz instrument and a mixture of $CD_3OD$ and $CDCl_3$ as solvent and TMS as internal standard. The $^1$H-NMR and $^{13}$C-NMR shift values for the compound are shown in Table 1. The values have been arranged into three groups, that is acyl, glycerol and sulphoquinovosyl moieties.

TABLE 1

NMR-values

| | $^1$H shift | $^{13}$C shift |
|---|---|---|
| Acyl moieties | | |
| C16 | 0.88(t) | 14.3 |
| C15 | | 23.4 |
| C14 | | 32.7 |
| C methylene | 1.25(m) | 29.9, 30.2, 30.5 |
| C3 | 1.59(m) | 25.7 |
| C2 | 2.3(b) | 34.8, 35.0 |
| C1 | | 173.7 |
| Glycerol moiety | | |
| sn-1* | 4.49(dd), 4.17(dd) | 64.0 |
| sn-2 | 5.3(m) | 71.3 |
| sn-3 | 4.08(dd), 3.57(dd) | 66.7 |
| Sulphoquinovosyl moiety | | |
| C1' | 4.81(d) | 99.0 |
| C2' | 3.40(dd) | 73.0 |
| C3' | 3.62(t) | 74.6 |
| C4' | 3.10(t) | 74.6 |
| C5' | 4.05(m) | 69.4 |
| C6' | 3.34(dd), 2.94(dd) | 54.0 |

*sn refers to stereospecific numbering

Formulations

Oral Emulsion

An oil-in-water emulsion (batch size 250 g) was prepared with the following ingredients:

| Ingredients | % |
|---|---|
| Corn oil | 20.00 |
| CPL ®-Galactolipid | 1.70 |
| SQDG | 0.15 |
| Sucrose | 17.00 |
| Potassium sorbate | 0.20 |
| Ascorbyl palmitate | 0.02 |
| Ammonium phosphatides | 0.10 |
| Lemon flavour | 0.20 |
| Water | ad 100.00 |

The emulsifier (CPL®-Galactolipid, a lipid emulsifier manufactured by Scotia LipidTeknik AB, Sweden) and antioxidant were dispersed in the oil. Sucrose, preservative, flavour and water were mixed. The oil phase and the aqueous phase were preheated to 50° C. and then the oil was added to the aqueous phase under high shear mixing at 16,000 rpm for 3.5 min. The preemulsion was then homogenised at 80 MPa and 55° C. for 7 cycles (Mini-Lab 8.30 H; APV Rannie AS, Denmark). This formulation resulted in a milky emulsion. The daily dose of this emulsion is 10 ml.

The neutral vegetable corn oil can be replaced by for instance an oil rich in γ-linolenic acid, such as evening primrose oil, EPO, giving an emulsion comprising SQDG and PUFA.

| Topical formulation | |
|---|---|
| Ingredient | % |
| CPL ®-Galactolipid | 17.00 |
| SQDG | 2.00 |
| Metagin | 0.05 |
| Propagin | 0.01 |
| Water | ad 100.00 |

SQDG was dispersed in water containing the preservatives. After the addition of the galactolipids, prepared from oats, the mixture was alternatively vortexed and stirred giving a viscous dispersion apted for topical application.

Biological Tests

In vivo animal models to test for anti-psoriatic activity are few and inadequate. Therefore, models that focus on the different characteristics of the disease are frequently used. One possibility is to consider the reported immunological background of the disease and the fact that the immunosuppressive drug cyclosporin A shows excellent therapeutic effects in treatment of severe psoriasis to use a test model where the ability of a compound to suppress the immune system is studied. In Phytother. Res. 5, 234–236, 1991, Tuominen et al. report an enhancing effect of Calaguala on the prevention of rejection of skin transplants in mice.

The ability of Calaguala methanolic extract to retard rejection of skin grafts in mice was studied using an adaptation of a method described by Billingham et al., J. Exp. Biol. 28, 385–403, 1957. Mice were pre-treated with either Calaguala orally or subcutaneously or with cyclosporin A subcutaneously for two weeks whereafter they were grafted with skin from a donor mice of different strain. They were then examined daily for signs of rejection. The results show that the Calaguala methanolic extract administered in a dose of 500 mg/kg/day gave a significant enhancement of the rejection time as compared to untreated animals. The mechanism for this effect could be the same as for the clinical effects reported for treatment of psoriasis with Calaguala.

The inflammatory aspect of psoriasis can be studied by using arachidonic acid induced oedema in rat ear, Bosman, Skin. Pharmacol. 7, 324–334, 1994, and by using the rat paw oedema test, a classical way of expertimentally investigating the effect of different compounds in acute inflammation.

The inflammatory tests described below were performed with the methanolic extract obtained from Polypodium decumanum, as described above, the Calaguala extract, in order to evaluate an optional activity of the extract on psoriasis.

It has previously been shown that the Calaguala extract exhibits dose-dependent inhibition of leukotriene $B_4$ synthesis in human leucocytes. This inhibitory activity was found to be caused by the polyunsaturated fatty acids linoleic, linolenic and arachidonic acid. The activity of additional unsaturated fatty acids, such as oleic acid and eicosapentaenoic acid, was also examined in the model and were all found to exhibit comparable inhibitory patterns. Leukotriene $B_4$ is an inflammatory mediator isolated in abnormally high quantities in the psoriatic skin. See Vasange et al., Prostaglandins, Leukotrienes and Essential Fatty Acids 50, 279–284, 1994.

Rat Ear Oedema

The rat ear oedema test is aimed to be used for detection of drugs with topical anti-inflammatory activity. It is based on the work by Tonelli et al., Endocrinology 77, 625–634, 1965, but instead of using the carcinogenic croton oil as induced, ethyl phenyl propiolate (EPP) is applied topically on the rat ears. The oedema develops rapidly (about 30 minutes) and starts to decline after two hours. Several measurements can be made by using a special measuring device and the values obtained with application of both EPP and the drug to be investigated are compared to values obtained with EPP alone.

The mechanism of the EPP induced oedema is not completely understood but it is known that compounds with broad anti-inflammatory action, like steroidal anti-inflammatory drugs, are active in this assay. The oedema can also be induced by other agents, such as arachidonic acid, and in that specific case the oedema is believed to develop through the action of the phospholipid, inflammatory mediators, leukotrienes. They can also contribute to the EPP oedema.

The Calaguala methanolic extract was tested in this model on several occasions. It was applied either locally (dissolved in methanol or acetone) or orally. Representative experiments are presented below:

TABLE 2

| | Ear thickness | |
|---|---|---|
| Treatment | Number of ears treated | Mean decrease in oedema |
| None | 6 | 0 |
| Calaguala 400 μg/ear | 12 | 30% |
| Mepyramin | 6 | 44% |

The thickness of ears is measured after 2 hours. As positive control the antihistamine mepyramine (1 μg/ear) is used. The significance of the values obtained was determined by using Students t-test (one tailed analysis). For mepyramin the significance was $p<0.01$ and for Calaguala $p<0.001$.

TABLE 3

| | Ear thickness | |
|---|---|---|
| Treatment | Number of ears treated | Mean decrease in oedema |
| None | 20 | 0 |
| Topical Calaguala | 20 | 32% |
| Pre-treatment Calaguala | 20 | 32% |

The thickness of the ears was measured after 2 hours. One Calaguala group received the extract topically, 400 μg/ear, and another group had been pre-treated for two weeks with about 1000 mg/kg/d Calaguala in their drinking water. The significancies were $p<0.001$ for the local treatment and $p<0.005$ for the oral treatment (Students t-test, one tailed).

Rat Paw Oedema

The rat paw oedema test is a classical way of experimentally investigating the effect of different compounds in acute inflammation. The most commonly used inducer is carrageenan which is injected to the hind paw of male Spraque Dawley rats. The mechanism of the oedema development which culminates after three hours is not completely understood. In general, it is believed to involve stimulation of prostaglandin synthesis, a fact that is supported by the inhibitory activity of cyclo-oxygenase inhibitors in this assay. More recent data, however, indicate that additional mechanisms are involved in the oedema development. For example, it has been shown that early phase of the carrageenan induced rat paw oedema is partly dependent on PAF release (Caruso et al., Pharmacol. Res. 31(1), 67–72, 1995). PAF has also been found to potentiate the oedema induced by carrageenan and the known PAF receptor antagonist, BN 52021, is capable of abolishing this enhancement.

Several tests were performed with the methanolic Calaguala extract which was applied orally in doses 500–2000 mg/kg. As positive control the cyclo-oxygenase inhibitor Na-salicylate (200 mg/kg) was used. A representative study is presented below:

TABLE 4

Effect of Calaguala methanolic extract on rat paw oedema induced by carrageenan.

| Treatment | No. of animals | Mean decrease in oedema | Significance |
|---|---|---|---|
| None | 5 | — | — |
| Na-salicylate | 5 | 43% | p < 0.0005 |
| Calaguala 500 mg/kg | 5 | 19% | p < 0.05 |
| Calaguala 1000 mg/kg | 5 | 22% | p < 0.025 |
| Calaguala 2000 mg/kg | 5 | 21% | p < 0.05 |

The significancies were calculated using Students t-test (one tailed).

In another set of experiments rats were pre-treated for two weeks with Calaguala methanolic extract in their drinking water. No statistically significant decrease in the oedema formation was observed when the rats were challenged with carrageenan on day 14. This finding is well in line with the theory of PAF being involved in the early phase of the carrageenan induced oedema whereas the later phases would be aused by stimulation of prostaglandins.

The Calaguala extract has also been investigated for inhibitory activity on the enzyme cyclooxygenase using bovine seminal vessel microsomes (White et al., Prostaglandins 7, 123–9, 1974). Cyclooxygenase is the first enzyme in the reaction chain for conversion of arachidonic acid to prostaglandins. The extract failed to show any inhibitory activity in this assay. This could be the explanation to why the inhibition caused by Calaguala in the carrageenen induced rat paw oedema does not increase with increased concentrations of the extract: only a minor part of the oedema increase is caused by PAF and Calaguala is only capable of inhibiting that part leaving the increase prostaglandin production unaffected. Thus the concentration of 500 mg/kg is already sufficient to cause total inhibition of the PAF induced part.

Quantification of SQDG In Calaguala Methanolic Extract

Methanolic extract prepared from leaves of Polypodium decumanum has been analysed for its content of sulphonoglycolipid, SQDG.

5700 gram of finely ground plant material was extracted with methanol overnight, under stirring at room temperature. The process was repeated three times with a total of 35 liter methanol. The extract was filtered and dried and the yield was 337 gram, In order to get a detectable signal for SQDG the methanolic extract was subjected to a preliminary fractionation.

Initially the extract was dissolved in water and the lipids were separated from the polar components by partitioning to chloroform. The chloroform extract was thereafter applied on a Sephadex LH20 column which had been equilibrated with ethanol. The column was first eluted with ethanol and thereafter with methanol. SQDG was selectively enriched in the methanol fraction. The fractions eluting prior to the change of eluent was examined by NMR for the presence of SQDG but only minor traces could be detected.

The HPLC analysis was carried out by using a straight phase system with polyvinyl alcohol bonded silica column (T-column, 89° C., PVA-SIL, 250×4.6 mm, 5μm), a flow rate of 1 ml/min, a light scattering detector (Sedex 45) and a mobile phase with a gradient system with hexane, isopropanol, n-butanol, tetrahydrofuran, iso-octane, water and ammonium acetate.

Commercially available SQDG was used as external standard and regression analysis was used to obtain an equation for a straight line. This was then used to calculate the amounts of SQDG present in the extract.

The amount SQDG present in the Calaguala extract was determined to be 4 mg/g extract.

PAF Induced Exocytosis

In this test, which is also called the elastase assay, the effect of the extracts on inhibiting the exocytosis induced by PAF was examined. This model was used to guide the fractionation of the extracts or isolated compounds.

Cell preparation: Peripheral blood anti-coagulated with heparin was obtained from healthy volunteers at the University Hospital (in Uppsala, Sweden). After sedimentation with 10% Dextran T-500 (Pharmacia Fine Chemicals) for 30 min at 20° C. the supernatant was removed and centrifuged at 200×g for 30 min. The sediments were treated with one volume of ice-cold water for 21 s followed by the addition of 9 volumes of $Mg^{2+}$ and $Ca^{2+}$ free PBS in order to lyse the remaining erythrocytes. After centrifugation (200×g for 10 min at 4° C.) the leucocytes were suspended in PBS (containing $Mg^{2+}$ and $Ca^{2+}$ and Cytochalasin B, Serva, 5 μg/ml) at a concentration of $10-30\times10^6$ cells/ml.

The assay was performed as described by Tuominen et al., Planta Medica 58, 306–310 (1992). In short leucocytes were incubated at 37° C. in PBS containing 2.5% BSA together with SAAVNA (N-succinyl-L-alanyl-L-alanyl-L-valine-p-nitroanilide, Bachem), the inhibitor in different concentrations or the vehicle (max. 0.1% DMSO) and PAF (Bachem) for 10 min. Blank tubes without PAF were run in parallel. The reaction was stopped by the addition of 2% citric acid and after the centrifugation, the samples were measured in a UV spectrophotometer at 405 nm. The absorbance of the corresponding blank tube was subtracted from the sample and the inhibition of PAF induced elastase release was calculated as the relative increase in absorbance as compared to the vehicle. The samples were analyzed as 4–5 concentrations ranging from $10^{-3}$ M to $10^{-7}$ M. They were dissolved in 10% DMSO (the isolated compound) or cyclodextrin (BN 52021, used as a reference) and then diluted with the buffer. The final concentration of DMSO or cyclodextrin never exceeded 0.1%.

The dose response curve of the SQDG of the formula III, and of the PAF receptor antagonist ginkgolide BN 52021 is shown in FIG. 1. Each point represents the mean of 2–4 experiments, all performed in duplicate. The $IC_{50}$ value was determined to 10 μM for the compound of the invention and to 80 μM for BN 52021.

In another experiment, the activity of SQDG rich fractions of different origin, such as from Spirulina and from bladder-wrack, were compared to the activity of SQDG from Calaguala, but no differences could be observed.

In still another experiment different polar lipids were tested in the model. Compounds such as MGDG and DGDG showed no inhibitory activity in concentrations around the $IC_{50}$ of SQDG.

[$^3$H]PAF Binding Assay

The PAF induced exocytosis model described above is used for screening for PAF receptor antagonists since it is a rapid, reproducable and reliable so called functional assay for PAF. However, a number of other actions, like elastase inhibition or membrane stabilisation, would also result in an inhibitory effect in the model which consequently is not exclusive for PAF receptor antagonism. To elucidate if SQDG acts through PAF receptor antagonism in the neutrophil, a receptor binding model using [3H]PAF as the radioligand was used.

Neutrophils are the most abundant circulating white blood cells and are usually the first cells to respond to an infectious or inflammatory stimulus. They are capable of phagocytosing appropriately opsonized bacteria and may also upon stimulation with e.g. PAF, secrete potentially toxic oxygen metabolites and lysosomal enzymes, including elastase, into the supernatant medium. These cells can also adhere to vascular endothelium and migrate towards the source of the chemoattractants. All these properties are a part of the response of the organism to inflammatory or infectious disturbance.

Cell preparation: For the receptor binding experiments the cells were prepared in the same way as described above except that concentrated suspensions of human leukocytes in a CDP-adenine solution were used and in the final step the cells were suspended in the incubation buffer and the cell count was adjusted to $3.1\times10^6$ cells/ml.

[$^3$H]PAF ($C_{18}$; 1-O-[$^3$H]octadecyl-2-acetyl-sn-3-phosphocholine; Amersham, England) receptor binding was studied in human polymorphonuclear leukocytes ($2.5\times106$ cells/ml) using a method recently reevaluated by us (Vas änge et al., in press, 1996). Incubations were performed for 120 min at 20° C. in a total volume of 1.0 ml containing 0.6 nM $Na_2HPO_4$, 0.6 nM $NaH_2HPO_4$ 25 mM Tris HCl, 130 mM NaCl, 5.5 mM KCl, 1.4 mM $CaCl_2$, 0.7 mM $MgCl_2$, 10 mM glucose, 0.5% BSA and 0.35–0.40 nM [$^3$H]PAF. Final pH was 7.0 at the incubation temperature used. Non-specific binding was determined with 1 μM C16-PAF (Bachem, Switzerland). The incubation contents were rapidly filtered by vacuum over Whatman GF/C glass-fibre filters using a 12 well Skatron Cell Harverster (Skatron A/S, Norway) and washed with 3×2 ml incubation buffer containing 0.1% BSA. The filtration took less than 15 s. Filters were also pre-soaked with incubation buffer containing 0.1% BSA. Following filtration, the filters were dried in an oven at 70° C. for 30 min and equilibrated for two hours in the scintillation vials before counting in a Packard scintillator at an efficiency of 55%. The competition binding assays were performed in triplicate in several concentrations ($10^{-11}$-$10^{-3}$ M) of the isolated compound and the receptor antagonists BN 50730 and BN 52021 as references. The compound and BN 50730 were dissolved in 100% DMSO ($10^{-2}$ M), BN 52021 in cyclodextrin and then further diluted with the incubation buffer.

Figure 2:
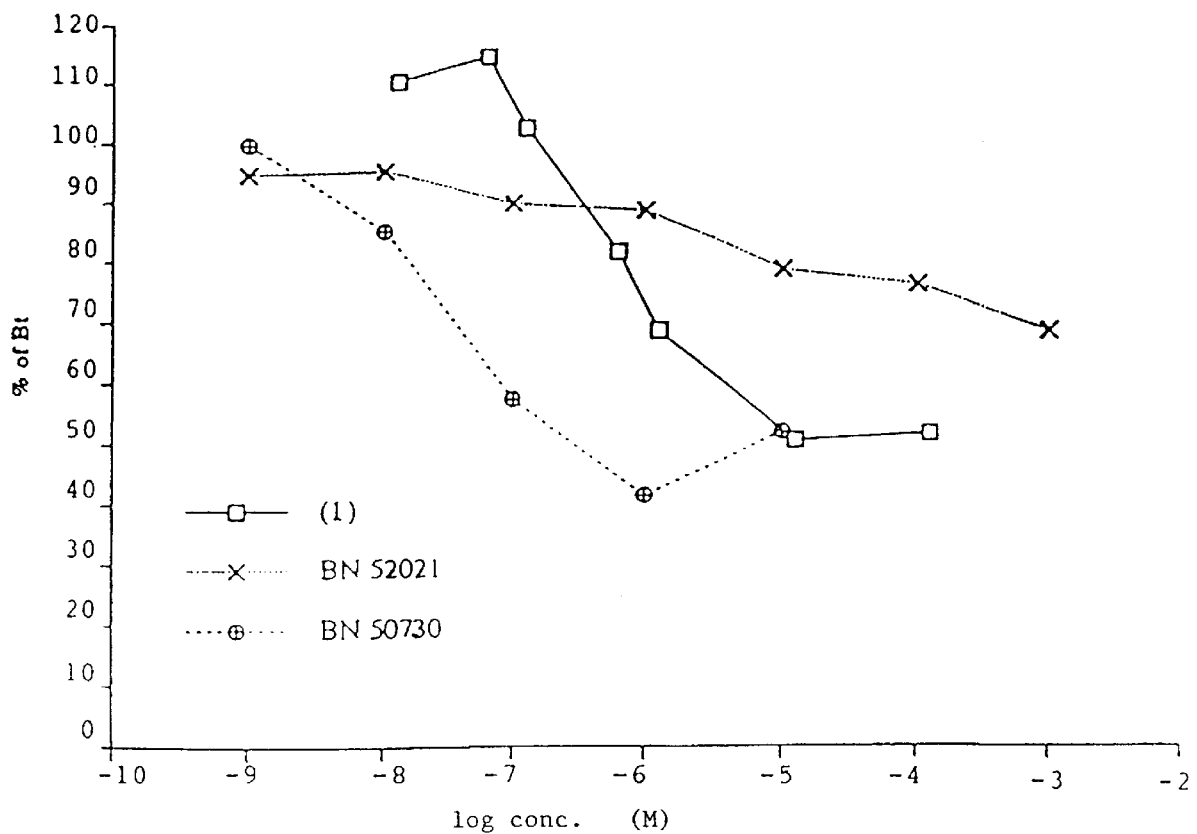
FIG. 2 shows the displacement curves of the ginkgolide BN 52021, the PAF receptor antagonist BN 50730, and of the SQDG compound of the formula III.

The displacement curves of the ginkgolide BN 52021, the hetrapazine-derived PAF receptor antagonist BN 50730 and of the SQDG compound of the formula III are presented in FIG. 2. The figure shows the decrease on dpm measured as percentage of total bound ligand (Bt). The level of non-specific binding was determined to about 45% of the Bt. Each point represents the mean of 2–4 experiments, all performed in triplicate. The $IC_{50}$ value was determined to be 2 μM for the isolated compound, 25 μM for BN 52021 and 0.04 μM for BN 50730.

SUMMARY

Calaguala has in clinical trials been shown to have beneficial effects in the treatment of psoriasis. One of the pathological findings in the psoriatic skin is elevated amounts of the inflammatory mediator platelet activating factor. The crude methanolic extract of Calaguala which gave the effects in psoriasis also shows a dose dependent inhibition of the PAF induced elastase release in human neutrophils, which is a functional assay for PAF receptor antagonism. When activity guided fractionation of the Calaguala extract was carried out, the main compound responsible for the PAF activity was discovered to be SQDG. SQDG was also proven to act through binding to PAF receptors in human neutrophils indicating a true receptor antagonistic property. Thus SQDG is believed to have therapeutic potential in treatment of diseases, such as inflammatory skin diseases. Another pathological finding in the psoriatic skin is elevated amounts of leukotriene $B_4$ which is known to be inhibited by polyunsaturated fatty acids. The combination of unsaturated fatty acids and SQDG, as in the Calaguala extract, should therefore be beneficial in the treatment of skin inflammation.

What is claimed is:

1. A method for the treatment or prophylaxis of inflammatory skin diseases or disorders in a mammal in need of thereof comprising administering to the said mammal a pharmaceutical composition comprising an SQDG having the formula

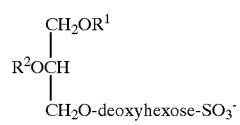

(I)

wherein $R^1$ and $R^2$, which are the same or different, are hydrogen or saturated or unsaturated, optionally hydroxy-substituted acyl groups, protonated or as a salt.

2. A method according to claim 1 wherein said SQDG has the formula

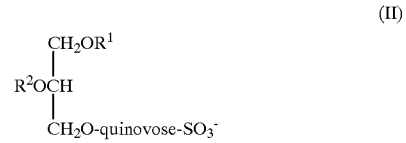

(II)

wherein $R^1$ and $R^2$, which are the same or different, are hydrogen, acetyl or acyl groups comprising 14–22 carbon atoms, preferably 16–18, and having up to 6 unsaturations, preferably 0–3.

3. A method according to claim 1 wherein said SQDG has the formula

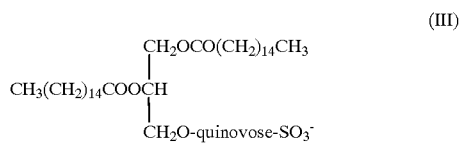

(III)

protonated or as a salt.

4. A method according to claim 1 wherein said inflammatory skin disease or disorder is selected from the group consisting of atopic dermatitis, urticaria and psoriasis.

5. A method according to claim 1 wherein said inflammatory skin disease is a proliferative disease.

6. A method according to claim 1 wherein said pharmaceutical composition further comprises said SQDG in combination with a polyunsaturated fatty acid in the form of free fatty acids, monoacylglycerols, diacylglycerols or triacylglycerols.

7. A method according to claim 6 wherein said inflammatory skin disease or disorder is psoriasis.

8. A method according to claim 6 wherein said polyunsaturated fatty acid is linoleic acid or linolenic acid.

* * * * *